United States Patent [19]

Seitz et al.

[11] Patent Number: 4,548,907
[45] Date of Patent: Oct. 22, 1985

[54] FLUORESCENT FLUID DETERMINATION METHOD AND APPARATUS

[75] Inventors: William R. Seitz; Zhang Zhujun, both of Durham, N.H.

[73] Assignee: Allied Corporation, Morristown, N.Y.

[21] Appl. No.: 531,957

[22] Filed: Sep. 14, 1983

[51] Int. Cl.[4] ...................... G01N 21/64; G01N 21/80
[52] U.S. Cl. ..................................... 436/163; 422/68; 436/133; 436/172; 436/178
[58] Field of Search ................. 436/163, 172, 68, 178, 436/133; 422/68, 52; 128/635, 632

[56] References Cited

U.S. PATENT DOCUMENTS

| | | | |
|---|---|---|---|
| 3,854,050 | 12/1974 | Peterson et al. | 250/429 |
| 3,994,302 | 11/1976 | Brennen | 128/784 |
| 4,174,384 | 11/1979 | Ullman et al. | 436/816 X |
| 4,194,877 | 3/1980 | Peterson | 8/4 |
| 4,200,110 | 4/1980 | Peterson et al. | 128/634 |
| 4,215,940 | 8/1980 | Lubbers et al. | 356/402 |
| 4,221,567 | 9/1980 | Clark et al. | 128/635 X |
| 4,241,738 | 12/1980 | Lubbers et al. | 128/666 |
| 4,269,516 | 5/1981 | Lubbers et al. | 356/427 |
| 4,306,877 | 12/1981 | Lubbers | 23/230 R |
| 4,344,438 | 8/1982 | Schultz | 128/634 |

FOREIGN PATENT DOCUMENTS

| | | | |
|---|---|---|---|
| 0039243 | 4/1981 | European Pat. Off. | 128/635 |
| 0003694 | 1/1976 | Japan | 436/164 |

OTHER PUBLICATIONS

Bunzo, Chemical Abstracts, vol. 68, 1968, No. 8944k.
Giusiani et al., Chemical Abstracts, vol. 98, 1983, No. 98:138549r.
Zhang et al., Chemical Abstracts, vol. 100, 1984, No. 100:180179e.
Fountaine et al., Analytical Chemistry, vol. 46, No. 1, Jan. 1974, pp. 62–66.
Parker et al., "Photoluminescence of Solutions", pp. 328–341, (1968).
Peterson et al., "Fiber Optic pH Probe for Physiological Use", Analytical Chem., vol. 52, No. 6, pp. 864–869, (1980).
Peterson et al., "A Miniature Fiberoptic pH Sensor Potentially Suitable for Glucose Measurements", Diabetes Care, vol. 5, No. 3, pp. 272–274, (1982).
Saari et al., "pH Sensor Based on Immobilized Fluoresceinamine", Analytical Chem., vol. 54, No. 4, pp. 821–823, (1982).
Giuliani et al., "Reversible Optical Waveguide Sensor for Ammonia Vapors", Optics Letters, vol. 8, No. 1, pp. 54–56, (1982).

Primary Examiner—Arnold Turk
Attorney, Agent, or Firm—Lowell H. McCarter

[57] ABSTRACT

A fluorescence-based optical sensor includes a membrane immobilized fluorophor secured to one end of a bifurcated fiber optic channel for exposure to the sample to be analyzed. The fiber optic channel also has an input end coupled to a radiation source arranged to supply radiation at two different wavelengths and an output end coupled to a bandwidth limited photosensor. The radiation source alternately excites the fluorophor at a first wavelength that excites an acid form of the fluorophor and at a second wavelength that excites a base form of the fluorophor, and a ratio of the resulting fluorescence intensities is taken as a measure of a characteristic of the sample being analyzed.

18 Claims, 7 Drawing Figures

FLUORESCENT FLUID DETERMINATION METHOD AND APPARATUS

This invention relates to fluid analysis, and more particularly to fluid analysis technology using fluorescence type sensors.

A determination of pH is desirable in a wide variety of biological studies. Previous pH sensors have included sensors of the electrochemical electrode type and optical (including absorbance based and fluorescence based) pH sensors with an optically sensed pH sensitive dye indicator. An absorbance-based optical pH sensor for in vivo use is disclosed in Peterson et al., U.S. Pat. No. 4,200,110. Saari and Seitz, "pH Sensor Based on Immobilized Fluoresceinamine", *Analytical Chemistry*, 1982, 54:821-823, described a pH sensor that uses fluoresceinamine and a single excitation wavelength. Such sensors are subject to errors based, for example, on interferences from species present in the sample which quench the fluorescence of the fluorophor or on the degradation of the fluorophor over time.

In accordance with one aspect, the invention features a fluorescence-based optical sensor which includes an immobilized pH-sensitive fluorophor, means for exposing the fluorophor to a sample to be analyzed, means for exciting the fluorophor at first and second wavelengths, detector means for sensing the intensity of the fluorescence emitted by the excited fluorophor, and means for taking the ratio of the intensities of fluorescence as sensed by the detector means as a measure of a characteristic of the sample being analyzed.

The invention takes advantage of relationships between the acid and base forms of the pH-sensitive fluorophor (HB and $B^-$, respectively) and between the ground and excited state of the fluorophor. The relationships between the forms of the fluorophor can be expressed by the following diagram:

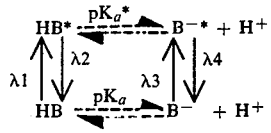

where $HB^*$ and $B^{-*}$ represent the acid and base forms, respectively, in the excited state, and $K_a$ and $K_a^*$ are the dissociation constants of the fluorophor in the ground and excited states, respectively. When HB absorbs radiation at its excitation wavelenght $\lambda 1$, the excited state of the acid form, $HB^*$, emits fluorescence of wavelength $\lambda 2$. When $B^-$ absorbs radiation at its excitation wavelength $\lambda 3$, it emits fluorescence at $\lambda 4$. In the excited state, if $HB^*$ ionizes at a rate equal to or greater than the rate at which it emits fluorescence, it also ionizes the produce $H^+$ and $B^{-*}$; $B^{-*}$ then emits fluorescence at $\lambda 4$.

Since the relative amounts of the acid and base forms of the fluorophor are pH-dependent, by taking the ratio of the fluorescence intensities measured at $\lambda 4$ using both excitation wavelengths $\lambda 1$ and $\lambda 3$, or the ratio of the fluorescence intensities measured at $\lambda 2$ and $\lambda 4$ using an excitation wavelength of $\lambda 1$, the resulting pH determining intensity ratio is insensitive to factors such as source intensity variations, fluorescence quenching, and slow loss of degradation of the fluorophor which affect the absolute intensity values measured. The sensor can thus be used in solutions which may contain species which interfere with the fluorescence emission and can be used over an extended period of time without giving erroneous readings.

The sensor can be adapted for use in a variety of pH ranges by choosing a fluorophor with an appropriate $pK_a$. The fluorophor can be used in the sensor in a variety of forms, including being immobilized on an ion exchange membrane, being contained in the interior of a pouch-like membrane which is permeable to the hydrogen ions in the liquid sample but not to the fluorophor itself, being attached to an ion exchange resin, or otherwise being in a form which allows the fluorophor to be brought into contact with the liquid sample without the ionization of the fluorophor being significantly interfered with and without the fluorophor being lost by dissolution or other chemical reaction into the liquid sample. The excitation and emission wavelengths used will depend on the excitation and emission spectra of the acid and base forms of the fluorophor. For example, the acid and base forms can be excited at different wavelengths, and intensities of fluorescence can be measured at the same wavelength for both excitations. Or, the acid and base forms can be excited at the same wavelength (if the excitation spectra of the two forms overlap sufficiently), and the intensities of fluoroscence can be measured at two different wavelengths (the emission wavelength of the acid form and the emission of the base form) to obtain the two intensity values necessary to take to ratio.

The sensor can be adapted for other uses, for example as a $CO_2$ sensor by securing the immobilized fluorophor at the end of a reservoir of bicarbonate solution and disposing a $CO_2$-permeable mebrane over the fluorophor. When such a sensor is placed in contact with a sample solution to be analyzed, the $CO_2$ in the sample will diffuse through the $CO_2$-permeable membrane into the bicarbonate reservoir. The resulting equilibrium between the $CO_2$ in solution and the bicarbonate in the reservoir will cause the pH of the solution to change, which change is sensed by the immobilized fluorophor; the resulting pH measurement providing a measure of the amount of $CO_2$ in the sample.

Preferred fluorophors are sulfonated aromatic acids such as 4,5-dihydroxynaphthalene-2,7-disulfonic acid; 3,4-dihydroxy-9,10-dioxo-2-anthracene-sulfonic acid; pyrogallolsulfonephthalein; and 9-carboxy-10-anthracene sulfonic acid. Preferably the flurophor has a pK that decreases at least three pH units on excitation, and the reaction rate of the flurophor is such that equilibrium of the flurophor in the excited state is essentially completely established before the excited fluorophor fluoresces. In particular embodiments, 8-hydroxy-1,3,6-pyrenetrisulfonic acid is employed as the fluorophor and is immobilized on an anion exchange membrane; the fluorophor being directly exposed to the sample to be analyzed in a pH sensor device and being juxtaposed with a silicone rubber membrane in a $CO_2$ sensor device. In those embodiments, the fluorophor is excited at wavelengths of 405 and 470 nm and fluorescense is sensed at 510 nm, the exciting sources and the detector being external to the analysis chamber and communicating with that chamber by fiber optic structure.

In those particular embodiments, the optical pH sensor includes a bifurcated fiber optic whose branched ends are connected respectively to a multi-wavelength light source and a narrow bandwidth detection system. Secured on the common end of the bifurcated fiber optic is an ion exchange membrane to which the pH-sensitive fluorophor (8-hydroxy-1,3,6-pyrene-trisulfonic acid) is electrostatically bound. With the fluorophor immobilizing membrane immersed in the sample solution, fluorescence intensity $I_{Fa}$ is measured at an emission wavelength $\lambda_e$ (510 nm) using a 405 nm wavelength $\lambda_a$ to excite the acid form of the fluorophor, the fluorescence intensity $I_{Fb}$ is measured at the same emission wavelength $\lambda_e$ using a 470 nm wavelength $\lambda_b$ to excite the base form of the fluorophor, and the ratio of $I_{Fb}/I_{Fa}$ is taken as a measure of the pH of the sample.

This embodiment of the invention is particularly useful for measuring physiological pH's based on the fluorescence of the trisodium salt of 8-hydroxy-1,3,6-pyrene-trisulfonic acid (HOPSA), as HOPSA has a $pK_a$ of 7.3, in the middle of the physiological pH range, and as HOPSA is conveniently and essentially irreversibly immobilized on anion exchangers as it has three sulfonate groups on an otherwise hydrophobic structure.

Other features and advantages of the invention will be seen as the following description of particular embodiments progresses, in conjunction with the drawing, in which.

DESCRIPTION OF PARTICULAR EMBODIMENTS

Figure 1:
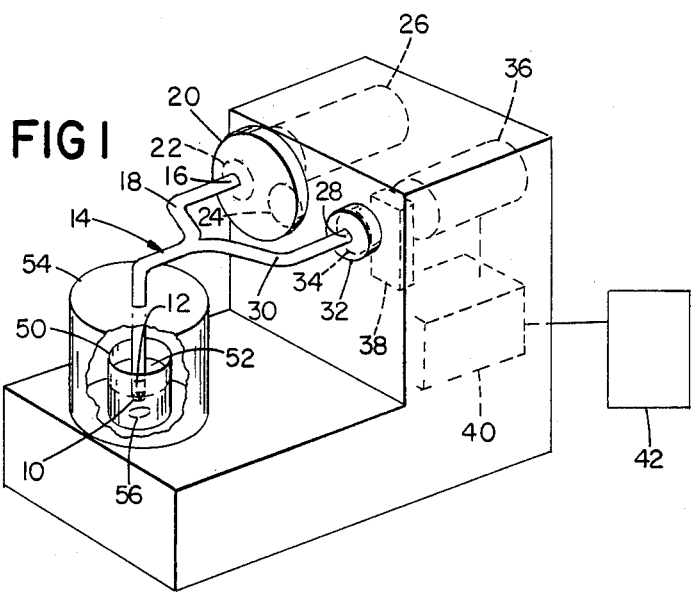
FIG. 1 is a diagrammatic view of a particular embodiment of the invention.

The sensor system shown in FIG. 1 includes membrane 10 secured at the common end 12 of bifurcated fiber optic channel 14. The end 16 of channel branch 18 is threadedly secured to filter wheel holder 20, the filter wheel carrying filters 22, 24 for selective interposition in the light path between light source 26 (a 250 watt, 5000 lumen tungsten halogen lamp) and channel branch 18; and the end 28 of channel branch 30 is threadedly secured to a similar filter holder 32 that carries filter 34 such that branch 30 of fiber optic channel 14 is optically coupled to photomultiplier sensor 36. Shutter 38 is interposed between holder 32 and sensor 36. The output of photomultiplier tube 36 is applied to processing circuitry 40 and the processor output is applied to appropriate output devices 42 such as a strip chart recorder and/or a display.

Figure 2:
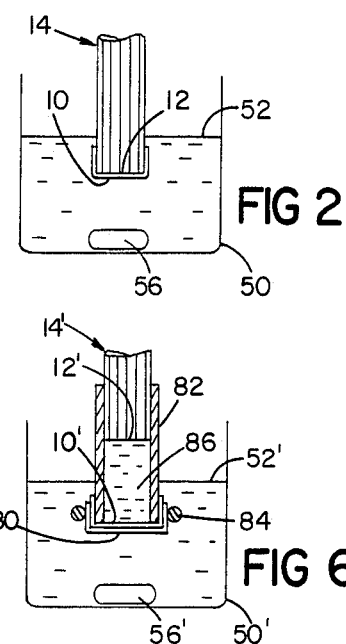
FIG. 2 is a diagrammatic view of the fluorophor immobilizing membrane secured on the common end of the fiber optic structure employed in the sensor of FIG. 1.

Membrane 10 carries an immobilized fluorophor and is secured on end 12 of fiber optic channel 14 (as indicated in FIG. 2) and is arranged to be disposed in a cuvette 50 that receives the sample 52 to be analyzed. Cuvette 50 is disposed in a light tight housing 54 through which the common end 12 of fiber optic channel extends for immersion of the immobilized fluorophor carrying membrane 10 in the sample liquid to be analyzed. A stirrer 56 is in the base of cuvette 50.

Membrane 10 is prepared by immersing an ion exchange membrane (RAI Research Company R-1035) in a solution of the fluorophor—the trisodium salt of the 8-hydroxy-1,3,6-pyrenetrisulfonic acid (HOPSA)—for twenty-four hours. The amount of the fluorophor immobilized per square centimeter of membrane 10 may be controlled by varying the concentration of the fluorophor in the initial solution.

In use, membrane 10 with the immobilized HOPSA fluorophor is submerged in sample liquid 52 in cuvette 50 and the fluorophor is alternately excited with radiation at 405 nm (filter 22) and radiation at 470 nm (filter 24). The resulting fluorescence of the fluorophor at 510 nm (filter 34) is sensed by photomultiplier tube 36 and the ratio of the two sensed fluorescence intensities is generated by processor 40 and applied to output device 42 as a measure of pH.

Figure 3:
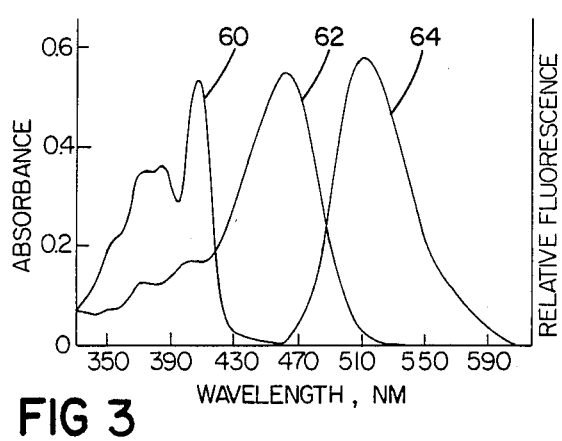
FIG. 3 is a graph showing the excitation and emission spectra of the immobilized fluorophor employed in the embodiment of FIG. 1.

FIG. 3 shows the excitation (absorption) and emission spectra of both the acid and base forms of the immobilized fluorophor. Curve 60 is the absorption spectrum of the fluorophor immersed in a 0.1M HCl solution; curve 62 is the absorption spectrum of the fluorophor immersed in a 2M KOH solution; and curve 64 is the fluorescence spectrum of the base form of the fluorophor (OPSA). As indicated in FIG. 2, both acid and base forms (OPSA and HOPSA) are excited at 405 nanometers while the base form (OPSA) is selectively excited at 470 nanometers.

Table 1 indicated effects of the amount of the HOPSA fluorophor bound to the membrane on fluorescence intensity.

TABLE 1

| EFFECT OF AMOUNT OF HOPSA ON INTENSITY* | | | | | |
|---|---|---|---|---|---|
| HOPSA ($\mu g/cm^2$) | 5.9 | 12.6 | 28.8 | 126 | 253 |
| Percent Absorbed 470 nm, pH 8.0 | 41 | 67 | 92 | 100 | 100 |
| pH 8.0, 470 nm Relative | 395 | 690 | 721 | 728 | 741 |
| pH 8.0, 405 nm Fluorescence | 127 | 222 | 241 | 243 | 245 |
| pH 6.0, 405 nm | 300 | 548 | 600 | 604 | 620 |

*Wavelengths refer to excitation wavelengths; values of percent light absorbed were determined using the absorbance data of FIG. 2.

As can be seen, fluorescence intensity increases with the amount of HOPSA immobilized per $cm^2$ up to a maximum value which is approached at an HOPSA loading of about 29 $\mu g/cm^2$; above this value fluorescence intensities increase only slightly. The data also shows that the relative fluorescence intensities essentially parallel the percent absorption, indicating that the inner filter effect is the primary factor influencing the variation in intensity with amount of bound fluorophor. The indicated lack of concentration quenching permits the use of membranes with heavy fluorophor loadings, which can be used for a prolonged period of time even with slow loss or decomposition of the fluorophor. In addition, heavy loadings limit the source radiation penetration through the membrane, so the presence of fluorophors in the sample will not interfere with the pH measurement.

Figure 5:
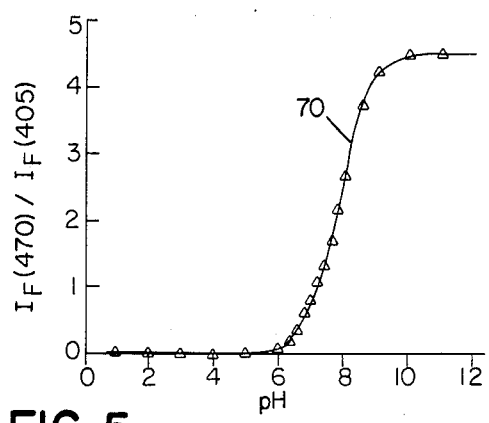
FIG. 5 is a graph showing the ratio of the relative fluorescence intensities vs. pH.
Figure 4:
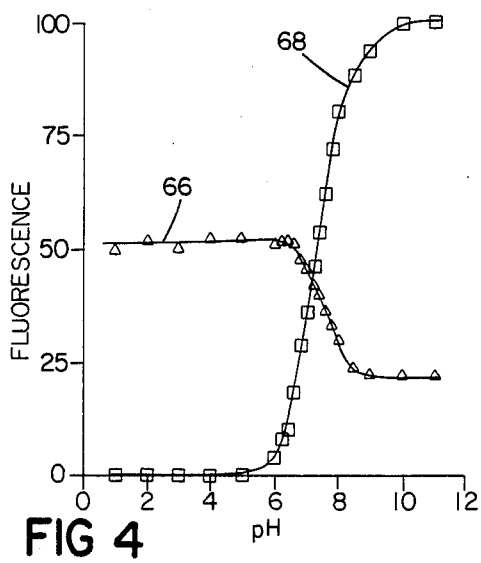
FIG. 4 is a graph showing the fluorescence intensity of the immobilized fluorophor vs. pH at excitation wavelengths of 405 nm and 470 nm.

FIG. 4 shows the relative intensity vs. pH for the immobilized HOPSA fluorophor excited at 405 nm (curve 66) and at 470 nm (curve 68). It can be seen that both the acid and base forms exhibit linear relationships between pH 6.0 and 8.0. By taking the ratio of the fluorescence intensities, sources of error (such as interfering species which quench the fluorescence, variations in source intensity, ionic strength of the solution, and slow loss or degradation of the fluorophor) are cancelled. Curve 70 of FIG. 5 shows the ratio vs. pH of the intensity of fluorescence measured at an excitation wavelength of 470 nm to the fluorescence intensity measured at an excitation wavelength of 405 nm. It can be seen that the working range for this particular embodiment (i.e., using HOPSA and the fluorophor) extends from about pH 6.0 to about pH 8.0, a range suitable for physiological applications. Fluorophors with other working pH ranges would be suitable for other applications.

Results of an examination of the stability of an immobilized HOPSA membrane examined over a 40 day period at a pH of 7.30 are summarized in Table 2. For each day, eleven measurements were made at pH 8.00 and 6.00, alternating between the two pH values. The relative standard deviation was 3.4% for pH 8.00 measurements and 3.7% for pH 6.00 measurements. This indicates that the carry over effect is small.

TABLE 2

OPERATIONAL STABILITY OF IMMOBILIZED HOPSA MEMBRANE

| Day | Relative Intensity |
|---|---|
| 1 | 100.0 |
| 2 | 97.8 |
| 3 | 100.9 |
| 5 | 101.9 |
| 10 | 99.0 |
| 15 | 99.0 |
| 20 | 100.9 |
| 25 | 100.9 |
| 30 | 99.0 |
| 35 | 97.1 |
| 40 | 93.2 |

The effects of certain inorganic cations and anions as well as oxygen and protein were investigated with solution of pH 7.30. Table 3 shows that the fluorescence intensity is essentially independent of species which could be encountered in a typical sample.

TABLE 3

INTERFERENCES OF INORGANIC IONS AND PROTEIN

| Added Species | Concentration (ppm) | Relative Intensity |
|---|---|---|
| None | — | 100.0 |
| $Ca^{+2}$ | 40 | 100.0 |
| $Mg^{+2}$ | 24 | 101.2 |
| $Fe^{+3}$ | 56 | 96.4 |
| $Al^{+3}$ | 27 | 98.5 |
| $Zn^{+2}$ | 65 | 102.2 |
| $Cu^{+2}$ | 63 | 100.0 |
| $Co^{+2}$ | 59 | 101.5 |
| $Ni^{+2}$ | 58 | 104.4 |
| $Cd^{+2}$ | 112 | 100.7 |
| $Pb^{+2}$ | 30 | 98.8 |
| $SO_4^{-2}$ | 500 | 102.3 |
| $PO_4^{-3}$ | 500 | 96.4 |
| $CO_3^{-2}$ | 500 | 99.5 |
| Acetate | 500 | 99.7 |
| Oxalate | 500 | 101.2 |
| Protein | 10% | 97.9 |
|  | 5% | 101.5 |

Effects of the presence and absence of oxygen are summarized in Table 4. Oxygen was removed from the sample by bubbling nitrogen gas ($N_2$) through the sample solution for various amounts of time, as shown below. Oxygen was added by bubbling oxygen gas ($O_2$) through the sample solution for various periods of time, also as shown below. It can be seen that neither the presence nor absence of oxygen significantly influenced the fluorescence intensities for immobilized HOPSA.

TABLE 4

| | EFFECT OF OXYGEN | | | |
|---|---|---|---|---|
| HOPSA ($\mu g/cm^2$): | 12.6 | | 28.8 | |
| pH: | 6.00 | 8.00 | 6.00 | 8.00 |
| Relative Intensity, $N_2$ pass min. | | | | |
| 0 | 100.0 | 100.0 | 100.0 | 100.0 |
| 10 | 100.1 | 100.1 | 99.6 | |
| 20 | 98.4 | 100.1 | 95.3 | 107.2 |
| 30 | 98.1 | 101.0 | 103.1 | 95.9 |
| Relative Intensity, $O_2$ pass min. | | | | |
| 10 | 97.1 | 100.0 | | |
| 20 | 100.0 | 98.2 | 97.0 | 105.1 |
| 30 | 98.3 | 100.1 | 97.4 | 100.4 |

Results of pH value determinations of serum samples with the apparatus shown in FIG. 1 are summarized in Table 5.

TABLE 5

| ANALYTICAL RESULTS OF pH IN SERUM | |
|---|---|
| Sample | pH* |
| 1 | 7.32 ± 0.08 |
| 2 | 7.40 ± 0.02 |
| 3 | 7.35 ± 0.03 |

*Average pH value of 11 trials ± standard deviation.

Figure 6:
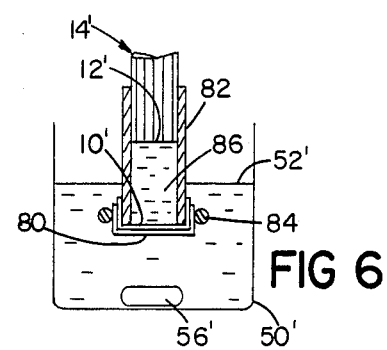
FIG. 6 is a diagrammatic view of portions of another embodiment for measuring carbon dioxide.
Figure 7:
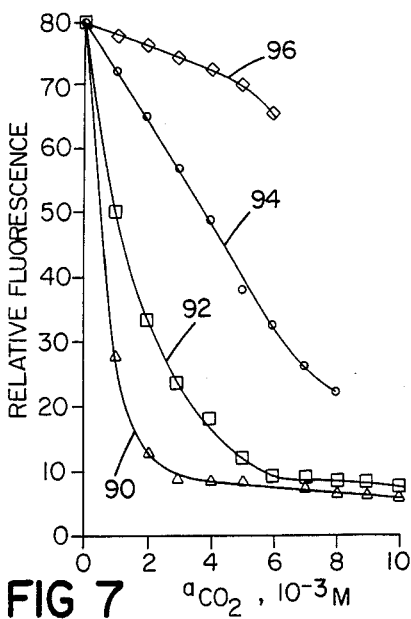
FIG. 7 is a graph showing fluorescence intensities vs. carbon dioxide at four different bicarbonate concentrations in the device shown in FIG. 6.

FIG. 6 shows a sensor system designed for measuring carbon dioxide. pH sensitive membrane 10' (loaded with 12.6 micrograms of HOPSA per square centimeter) and carbon dioxide permeable silicone rubber membrane 80 are secured the end of glass tube 82 by suitable securing means such as O-ring 84. Glass tube 82 is filled with a bicarbonate solution 86 of known concentration and the common end 12' of fiber optic channel 14' is received within tube 82, channel 14' being coupled to a radiation source and sensor arrangement of the type shown in FIG. 1. The concentration of the internal bicarbonate solution 86 should be chosen so that the carbon dioxide concentration of interest yields pH changes between 6.5 and 8.0. Factors influencing response time of this sensor include the rate of diffusion of carbon dioxide through the silicon membrane 80 and the pH sensitive membrane 10'. The graph of FIG. 7 indicates fluorescence intensity responses of the system shown in FIG. 6 as a function of carbon dioxide concentration. A standard sodium bicarbonate solution 86 was inserted into the chamber bounded by the end of channel 12', membrane 10' and tube 82 and a fixed volume (4.5 milliliters) of carbon dioxide free acid reagent was piped into cuvette 50'. After stirring for two minutes, the fluorescence intensity was measured, the fiber optic channel 12' being excited at 470 nanometers and emission being observed at 510 nanometers. Fluorescence intensity responses of the system shown in FIG. 6 as a function of carbon dioxide concentration for different bicarbonate concentrations are shown in the graph of FIG. 7: curve 90—$10^{-4}$ M $NaHCO_3$ concentration, curve 92—$10^{-3}$ M $NaHCO_3$ concentration, curve 94—$10^{-2}$ M NaHCO$_3$ concentration, and curve 96—$10^{-1}$ M NaHCO$_3$ concentration.

While particular embodiments of the invention have been shown and described, various modifications will be apparent to those skilled in the art, and therefore it is not intended that the invention be limited to the disclosed embodiments or to details thereof and departures may be made therefrom within the spirit and scope of the invention.

What is claimed is:

1. A fluorescence-based optical sensor comprising
   a fluorophor having an acid form and a base form, the relative amounts of said acid and base forms being pH dependent,
   means for exposing said fluorophor to a sample to be analyzed,
   means for exciting said fluorophor at first and second wavelengths, said first wavelength exciting said acid form of said fluorophor and said second wavelength exciting said base form of said fluorophor,
   detector means for sensing at a single wavelength the intensities of fluorescence of said fluorophor when said fluorophor is excited at said first wavelength and at said second wavelength, and
   means for taking the ratio of the intensities of fluorescence at said single wavelength as sensed by said detector means as a measure of a characteristic of the sample being analyzed.

2. The sensor of claim 1 wherein said fluorophor has a pK that decreases at least three pH units on excitation.

3. The sensor of claim 1 wherein the reaction rate of said fluorophor is such that equilibrium of said fluorophor in the excited state is essentially completely established before said excited fluorophor fluoresces.

4. The sensor of claim 1 further including means for immobilizing said fluorophor.

5. The sensor of claim 4 wherein said means for immobilizing said fluorophor includes an ion exchange membrane to which said fluorophor is electrostatically bound.

6. The sensor of claim 5 wherein said fluorophor is 8-hydroxy-1,3,6-pyrenetrisulfonic acid.

7. The sensor of claim 1 wherein said fluorophor is a sulfonated aromatic acid.

8. The sensor of claim 7 wherein said fluorophor is selected from the group consisting of 4,5 dihydroxynaphthalene - 2,7 disulfonic acid; 3,4dihydroxy - 9,10 - dioxo - 2 anthracene - sulfonic acid; pyrogallolsulfonephthalein; 9 - carboxy - 10 - anthracene sulfonic acid; and 8-hydroxy-1,3,6-pyrenetrisulfonic acid.

9. The sensor of claim 1 wherein said fluorophor has a pK that decreases at least three pH units on excitation, and the reaction rate of said fluorophor is such that equilibrium of said fluorophor in the excited state is essentially completely established before said excited fluorophor fluoresces.

10. The sensor of claim 9 and further including an anion exchange membrane to which said fluorophor is electrostatically bound.

11. The sensor of claim 10 and further including fiber optic structure having a first end and a second end, said second end being bifurcated into a first branch and a second branch, said first branch being coupled to said exciting means, said second branch being coupled to said detector means, and said anion exchange membrane being coupled to said first end.

12. The sensor of claim 11 and further including chamber structure secured to said first end of said fiber optic structure, a selectively permeable barrier membrane secured to said chamber to allow permeation of carbon dioxide into said chamber, and material in said chamber having a pH that changes as a function of the species to which said barrier membrane is permeable, said anion exchange membrane being secured to said chamber structure for exposure to said material in said chamber.

13. The sensor of claim 12 wherein said anion exchange membrane and said selectively permeable barrier membrane are secured in juxtaposed relation across an open end of said chamber structure opposite said first end of said fiber optic structure.

14. The sensor of claim 13 wherein said selective permeable membrane is composed of silicone rubber and said material in said chamber is a bicarbonate solution.

15. A method of measuring a characteristic of a sample using an optical pH sensor,
    said sensor comprising a multi-wavelength light source, a limited bandwidth light detector, and a pH-sensitive fluorphor, said fluorophor having a first dissociation constant associated with the ground-state dissociation of said fluorophor into a hydrogen ion and the corresponding anion and a second dissociation constant associated with the excited-state dissociation, said second dissociation constant being several orders of magnitude larger than said first dissociation constant,
    said method comprising exposing said fluorophor to said sample, measuring the fluoroescence intensity $I_{Fa}$ at an emission wavelength $\lambda_e$ using the excitation wavelength $\lambda_a$ of the acid form of the fluorophor, measuring the fluorescence intensity $I_{Fb}$ at said $\lambda_e$ using the excitation wavelength $\lambda_b$ of the base form of the fluorophor, and taking the ratio of $I_{Fb}/I_{Fa}$ as a measure of a characteristic of the sample.

16. The method of claim 15 wherein said fluorophor is a sulfonated aromatic phenol.

17. The method of claim 16 wherein said fluorophor is 8-hydroxy-1,3,6-pyrenetrisulfonic acid.

18. The method of claim 17 wherein said fluorophor is immobilized on an anion exchange membrane, said $\lambda_e$ is 510 nm, said $\lambda_a$ is 405 nm, and said $\lambda_b$ is 470 nm.

* * * * *